US012636269B2

(12) United States Patent
Rathmacher et al.

(10) Patent No.: US 12,636,269 B2
(45) **Date of Patent: *May 26, 2026**

(54) COMPOSITIONS AND METHODS OF USE OF GAMMA-KETOALDHEYDE SCAVENGERS FOR TREATING, PREVENTING OR IMPROVING FIBROSIS OF THE LIVER

(71) Applicant: MTI Biotech, Inc.

(72) Inventors: John Rathmacher, Story City, IA (US); Naji Abumrad, Nashville, TN (US); Charles Flynn, Nashville, TN (US)

(73) Assignee: MTI Biotech, Inc., Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/213,416

(22) Filed: Jun. 23, 2023

(65) Prior Publication Data

US 2023/0330049 A1 Oct. 19, 2023

Related U.S. Application Data

(63) Continuation of application No. 17/064,154, filed on Oct. 6, 2020, now abandoned, which is a continuation-in-part of application No. 16/122,416, filed on Sep. 5, 2018, now abandoned.

(60) Provisional application No. 62/554,294, filed on Sep. 5, 2017.

(51) Int. Cl.

*A61K 31/197* (2006.01)
*A61K 31/137* (2006.01)
*A61P 1/16* (2006.01)

(52) U.S. Cl.

CPC .......... *A61K 31/197* (2013.01); *A61K 31/137* (2013.01); *A61P 1/16* (2018.01)

(58) Field of Classification Search

CPC ........ A61K 31/197; A61K 31/137; A61P 1/16
See application file for complete search history.

(56) References Cited

U.S. PATENT DOCUMENTS

| | | | | |
|---|---|---|---|---|
| 2014/0256774 A1* | 9/2014 | Roberts | A61P 25/00 | 514/351 |
| 2015/0265584 A1* | 9/2015 | Oates | A61K 45/06 | 514/567 |

FOREIGN PATENT DOCUMENTS

| | | | |
|---|---|---|---|
| CN | 103796648 | A | 5/2014 |
| EP | 210140 | A2 | 1/1987 |
| JP | 61239891 | A | 10/1986 |
| JP | 2014524918 | A | 9/2014 |
| WO | 2013010034 | A2 | 1/2013 |
| WO | 2017033119 | A1 | 3/2017 |
| WO | 2018048932 | A1 | 3/2018 |

OTHER PUBLICATIONS

Roychowdhury et. al. (Free Radical Biology and Medicine (2009) 47: 1526-1539) (Year: 2009).*

Longato et. al. (Free Radical Biology and Medicine (2017) 162-173 , available online Nov. 2016) (Year: 2016).*

Longato et. al. (UEG Journal (2014) 2(1S) A132-A605) (Year: 2014).*

Davies (Curr. Pharamcol. Rep. (Apr. 2017) 3:51-67) (Year: 2017).*

Washington et. al. (Hum. Pathol. (2000) 31:822-828),. (Year: 2000).*

Caligiuri et al. , "Activation of JNK modulates the profibrogenic actions of myostatin in hepatic stellate cells (HSC)", Oct. 1, 2014.

Gaens et al. , "Endongenous Formation of N-(carboxymethyl)lysine is Increased in Fatty Livers and Induces Inflammatory Markers in an in Vitro Model of Hepatic Steatosis", 2012.

Longato, Lisa , et al., "Reactive gamma-ketoaldehyde as novel activators of hepatic stellate cells in vitro", Free Radical Biology and Medicine, 102, Nov. 24, 2016, 162-173.

Longato , et al., "Role of gamma-ketoaldeyde as novel mediators of experimental fibrogenesis and stellate cells activation", United European Gastroenterology Journal, Dec. 30, 2014, A136.

Longato et al. , "Reactive gamma-ketoaldehydes as novel activators of hepatic stellate cells in vitro", Jan. 1, 2017.

Seki et al. , "Hepatic Inflammation and Fibrosis: Functional Links and Key Pathways", 2015.

Noureddin, M. , et al., "Review article: emerging anti-fibrotic therapies in the treatment of non-alcoholic steatohepatitis", Alimentary Pharmacology & Therapeutics, vol. 43, No. 11, Apr. 8, 2016, 1109-1123.

Zois, C.D. , et al., "Systematic review: hepatic fibrosis—regression with therapy", Alimentary Pharmacology & Therapeutics, Blackwell Scientific Publications Ltd, vol. 28, No. 10, Aug. 30, 2008, 1175-1187.

* cited by examiner

*Primary Examiner* — Marcos L Sznaidman

(74) *Attorney, Agent, or Firm* — Dentons Davis Brown; Emily Harris

(57) ABSTRACT

Methods and compositions for use in treating, attenuating, preventing or improving liver fibrosis in a subject are described. The compounds of the present invention are gamma-ketoaldehyde scavengers.

12 Claims, 2 Drawing Sheets

COMPOSITIONS AND METHODS OF USE OF GAMMA-KETOALDHEYDE SCAVENGERS FOR TREATING, PREVENTING OR IMPROVING FIBROSIS OF THE LIVER

This application is a continuation of U.S. application Ser. No. 17/064,154 filed Oct. 6, 2020, which is a continuation-in-part of U.S. application Ser. No. 16/122,416 filed Sep. 5, 2018, which claims priority to U.S. Application Ser. No. 62/554,294 filed Sep. 5, 2017 which is herein incorporated by reference in its entirety.

BACKGROUND OF THE INVENTION

1. Field

The present invention relates to a composition comprising a gamma-ketoaldehyde scavenging compound, such as 2-Hydroxybenzylamine (2-HOBA), and methods of administering a gamma-ketoaldehyde scavenger to treat, prevent, attenuate, reduce, slow the progression of, or improve fibrosis of the liver.

2. Background

Liver fibrosis is a histological change caused by liver inflammation and/or chronic injury. Damage to the liver causes liver stellate cells to become overactive and triggers the extra cellular matrix (ECM) synthesis to increase. Excess amounts of collagen fiber deposits occurs in the extracellular spaces of the liver cells which causes the liver cells to lose blood infusion and become hardened. Fibrosis is a common aspect of many liver diseases and is defined as the formation of scar tissue in the liver. Various etiologies give rise to hepatic fibrosis, including but not limited to hepatitis, nonalcoholic steatohepatitis (NASH), nonalcoholic fatty liver disease (NAFLD), toxins, alcoholic liver disease (ALD), genetic conditions, cholestatic disorders, and autoimmune diseases. Indicators of liver fibrosis included deposition of fibrotic tissue and activation of the fibrogenesis cascade. Fibrosis may produce permanent scarring of the hepatic tissue which is known as cirrhosis.

In the case of NASH, there are two hallmark histologic features: hepatic inflammation and fibrosis. While no FDA-approved therapeutics for NASH exist, several potential options have been investigated; the most promising of which include vitamin E, thiazolidinediones, and pentoxifylline. Each of these has shown some borderline clinical efficacy, but all are limited by their potential for side effects and/or toxicity, and importantly, none of these therapeutics have improved fibrosis, the strongest indicator of mortality in NASH.

γ-ketoaldehydes (γ-KA, also known as isolevuglandins or isoketals) are highly reactive lipid aldehydes that rapidly react with lysine residues and phosphatidylethanolamine to form adducts. γ-KA lipid and protein adducts have been observed in several animal models of liver disease as well as in humans with NASH. Preliminary data from humans with NASH also indicate elevated γ-KA-protein adduct formation in liver, and γ-KA-protein adducts similarly induce liver injury. γ-KA-protein adducts are linked to the loss of protein function, mitochondrial dysfunction, ER stress, and pro-inflammatory cytokine expression.

2-hydroxγ-benzylamine (2-HOBA or salicylamine), a staple of buckwheat, was found to be a potent scavenger of γ-KAs scavenging γ-KAs 980-fold faster than the rate of formation of γ-KA-protein adducts. Studies have shown that 2-HOBA is 980 times more reactive than lysine with γ-KAs. Importantly, they showed that this γ-KA scavenger does not inhibit cyclooxygenase enzymes. Studies have shown that 2-HOBA dramatically protected HepG2 cells against $H_2O_2$-induced cytotoxicity.

It has recently been found that γKAs induced activation of human hepatic stellate cells (HSCs) to a pro-inflammatory/pro-fibrogenic phenotype. HSCs, which make up −10% of resident liver cells, are quiescent in normal, healthy liver. However, in response to liver injury, HSCs become activated and transdifferentiate into proliferative, inflammatory myofibroblasts, which are characterized by enhanced extracellular matrix production. As such, activated HSCs are well-established as the major fibrogenic cells in the liver and are strongly implicated in the development hepatic fibrosis in states of chronic liver injury. Oxidative stress, particularly the products of lipid oxidation, has direct pro-inflammatory/pro-fibrogenic effects on HSCs. Longato et al. recently identified γKA as novel HSC activators by exposing primary human HSC to synthetic 15-$E_2$-isolevuglandin (15-E2-IsoLG). Exposure to non-cytotoxic levels of 15-$E_2$-IsoLG promoted HSC activation, as evidenced by upregulated α-SMA expression, MAPK activation, and increased cytokine production.

Without being bound by theory or mechanism, the present inventors have discovered that selective scavengers of γKAs attenuate, reduce, treat, slow the progression of and/or improve hepatic fibrosis. Further, the compositions of the present invention do not present the adverse effects or toxicity associated with existing therapeutics for treating liver diseases such as NASH.

The isoketal scavangers of the present invention are compounds such as salicylamine (SA), for example, and analogs thereof.

The present invention includes use of gamma ketoaldehyde scavengers, including 2-HOBA, to scavenge toxic oxidized lipids (ketoaldehydes) to treat, prevent, attenuate, reduce, slow the progression of, or improve fibrosis of the liver hepatic fibrosis.

SUMMARY OF THE INVENTION

Disclosed is a method for treating, preventing and/or attenuating hepatic fibrosis that comprises identifying a subject in need of treatment, prevention and/or attenuation of hepatic fibrosis, and administering to said subject an effective isoLG scavenging amount of at least on compound of the following formula:

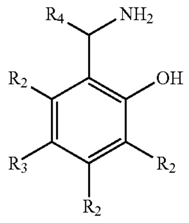

wherein $R_2$ is independently chosen from H, substituted or unsubstituted alkyl; $R_3$ is H, halogen, alkyl, alkoxy, hydroxyl, nitro; $R_4$ is H, substituted or unsubstituted alkyl, carboxyl; and pharmaceutically acceptable salts thereof.

In one embodiment, $R_2$ is independently chosen from H, ethyl, methyl. In another embodiment, the compound is 2-hydroyxbenzylamine, methyl-2-hydroyxbenzylamine, ethyl-2-hydroyxbenzylamine. In another embodiment, the compound is:

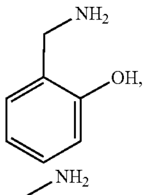,
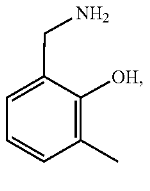,
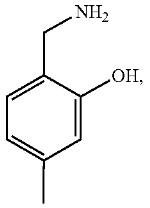,
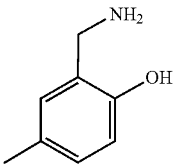
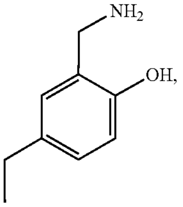, or
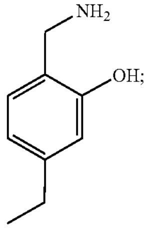;

or a pharmaceutically acceptable salt thereof.

In another embodiment, the compound is:

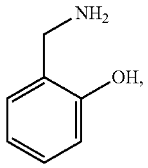,
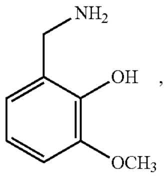,
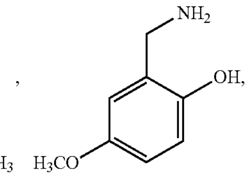,
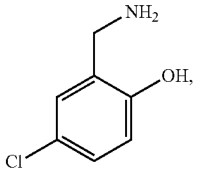,
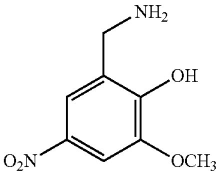,
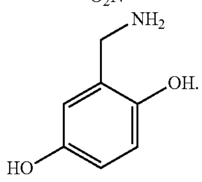.

Or a pharmaceutically acceptable salt thereof.

In one embodiment, the disclosed treating step inhibits the progression of hepatic fibrosis. In one embodiment, the disclosed treating step attenuates the severity of hepatic fibrosis. Also, in one embodiment, the disclosed treating step mitigates the damaging effects of hepatic fibrosis.

In another embodiment, the compound or pharmaceutically acceptable salt thereof is administered in a composition that comprises said compound or a pharmaceutically acceptable salt thereof and a pharmaceutically acceptable carrier.

One object of the present invention is to provide compositions used treat, prevent, attenuate, reduce, slow the progression of, and/or improve hepatic fibrosis.

Another object of the present invention is to provide a therapeutic or effect amount of a preparation of the compound of the present invention to treat, prevent, attenuate, reduce, slow the progression of, or improve the symptoms of hepatic fibrosis and/or reduces the severity of hepatic fibrosis symptoms.

A further object of the present invention includes providing a novel nutritional therapy that will treat, prevent, attenuate, reduce, slow the progression of, or improve fibrosis of liver fibrosis. The nutritional therapy can be used to improve overall liver health and support healthy liver function.

An additional object of the present invention includes providing compositions and methods of use of 2-HOBA, alternatively named Salicylamine, SAM, 2-hydroxybenzylamine, and pentylpyridoxamine (PPM).

DETAILED DESCRIPTION OF THE INVENTION

Figure 1A:
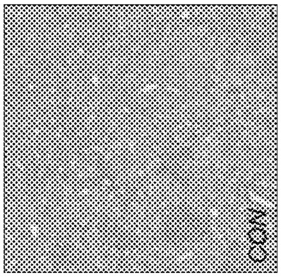
FIGS. 1*a* to 1*b* are images of slides depicting Picosirius Red staining of fibrosis in control and 2-HOBA treated mice.

All publications cited or mentioned herein are incorporated by reference to disclose and describe the methods and/or materials in connection with which the publications are cited.

The compositions described herein are used treat, prevent, attenuate, reduce, slow the progression of, and/or improve hepatic fibrosis.

A therapeutic or effect amount is a preparation of the compound of the present invention that treat, prevent, attenuate, reduce, slow the progression of, or improve the symptoms of hepatic fibrosis and/or reduces the severity of hepatic fibrosis symptoms.

The present invention includes a novel nutritional therapy that will treat, prevent, attenuate, reduce, slow the progression of, or improve fibrosis of liver fibrosis. The nutritional therapy can be used to improve overall liver health and support healthy liver function.

The present invention comprises a means to specifically prevent the formation of γKA—adducts in the liver using a class of bifunctional electrophile (BFE) “scavenger” molecules. A series of phenolic amines that includes pyridoxamine and its water soluble derivative 2-HOBA, a natural product of buckwheat seed comprise the preferred embodiment. 2-HOBA in particular reacts 980-fold faster with IsoLGs than with lysine, preventing protein and lipid adduction in vitro and in vivo.

The present invention incudes compositions and methods of use of 2-HOBA, alternatively named salicylamine, SAM, 2-hydroxybenzylamine, and pentylpyridoxamine (PPM).

Examples of compounds of the present invention include, hut are not limited to, compounds selected from the formula or analogs thereof, and pharmaceutical salts thereof:

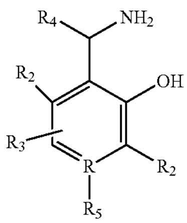

wherein:

R is N or C;

$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;

$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;

$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;

$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;

and stereoisomers and analogs thereof.

Another embodiment of the present invention includes compounds of the following formula, and their use in methods for treating, preventing, or ameliorating liver fibrosis to a subject with or at risk of liver fibrosis:

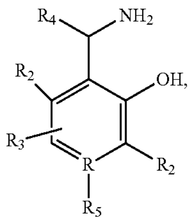

wherein:

R is N or C;

$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;

$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;

$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;

$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N; and stereoisomers and analogs thereof.

In certain embodiments, the compound may be selected from the compounds disclosed herein. In a preferred embodiment, the compound may be salicylamine. Other compounds that may be used include methyl-2-HOBA or ethyl-2-HOBA. The present invention includes administering to a patient in need thereof an effective amount of at least one isoLG scavenger compound of the present invention, or a pharmaceutically acceptable salt thereof.

Another embodiment of the present invention is a method for treating, preventing, or ameliorating liver fibrosis to a subject with or at risk of liver fibrosis, thereby inhibiting or treating the liver fibrosis, comprising the step of co-administering to the subject at least one compound in a dosage and amount effective to treat the dysfunction in the mammal, the compound having a structure represented by a compound of the following formula:

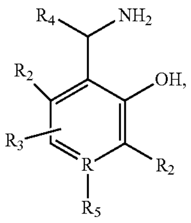

wherein:

R is N or C;

$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;

$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;

$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;

$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N; and stereoisomers and analogs thereof; with a drug having a known side effect of treating, preventing, or ameliorating liver fibrosis.

Examples of compounds that may be used with the methods disclosed herein include, but are not limited to, compounds selected from the formula:

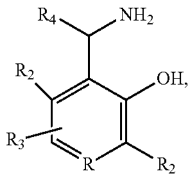

wherein:

R is N or C;

$R_2$ is independently H, substituted or unsubstituted alkyl;

$R_3$ is H, halogen, alkoxy, hydroxyl, nitro;

$R_4$ is H, substituted or unsubstituted alkyl, carboxyl; and pharmaceutically acceptable salts thereof.

Further example include compounds of the following formula:

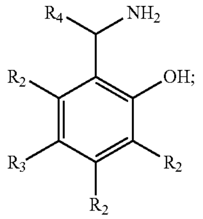

wherein: $R_2$ is independently chosen from H, substituted or unsubstituted alkyl; $R_3$ is H, halogen, alkyl, alkoxy, hydroxyl, nitro; $R_4$ is H, substituted or unsubstituted alkyl, carboxyl; and pharmaceutically acceptable salts thereof. In other embodiments, $R_2$ is independently chosen from H, ethyl, methyl.

In a preferred embodiment, the compound is salicylamine (2-hydroxybenzylamine or 2-HOBA).

The compound may be chosen from:

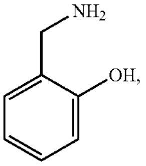 or 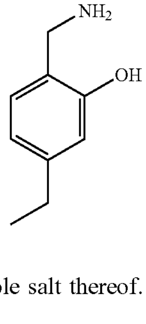

or a pharmaceutically acceptable salt thereof.

The compound may also be chosen from:

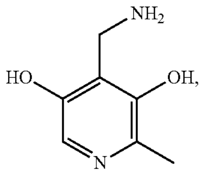
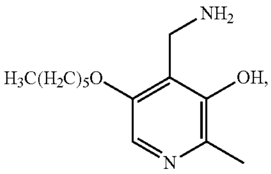
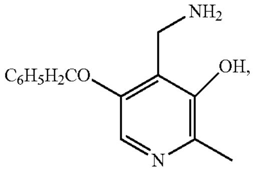
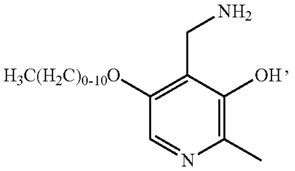
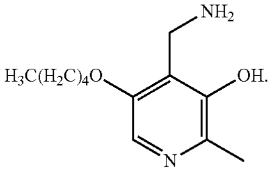

or a pharmaceutically acceptable salt thereof.

The compounds or analogs may also be chosen from:

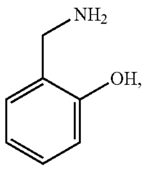
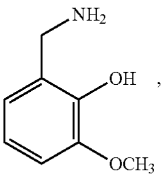 ,
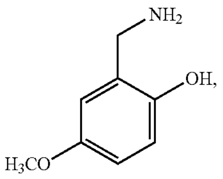
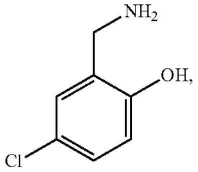
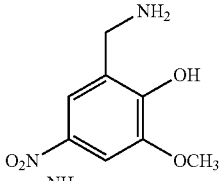 ,
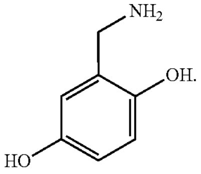

or a pharmaceutically acceptable salt thereof.

The compounds may also be chosen from:

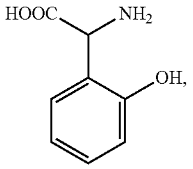
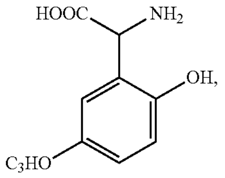
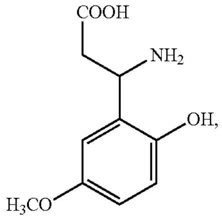

or a pharmaceutically acceptable salt thereof.

The compounds may also be chosen from

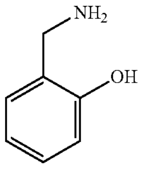

Salicylamine
(SA)

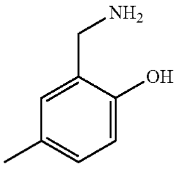

Methylsalicylamine
(MeSA)

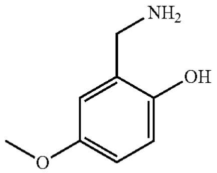

5-Methoxysalicylamine
(5-MoSA)

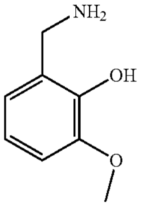

3-Methoxysalicylamine
(3-MoSA)

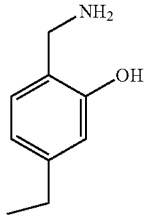

Ethylsalicylamine
(EtSA)

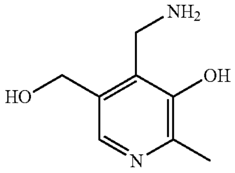

Pyridoxamine
(PM)

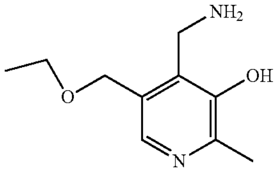

Ethylpyridoxamine
(EtPM)

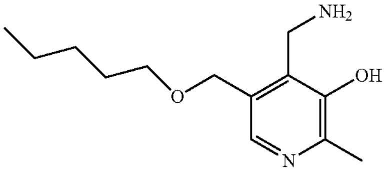

Pentylpyridoxamine
(PPM)

or a pharmaceutically acceptable salt thereof.

The compounds of the present invention can be administered by any method and such methods are well known to those skilled in the art and include, but are not limited to oral administration, transdermal administration, administration by inhalation, nasal administration, topical administration, intravaginal administration, ophthalmic administration, intraaural administration, intracerebral administration, rectal administration, and parenteral administration, including injectable administration such as intravenous administration, intra-arterial administration, intramuscular administration and subcutaneous administration. The compounds can be administered therapeutically, to treat an existing disease or condition, or prophylactically for the prevention of a disease or condition.

Although any suitable pharmaceutical medium comprising the composition can be utilized within the context of the present invention, preferably, the composition is combined with a suitable pharmaceutical carrier, such as dextrose or sucrose.

Methods of calculating the frequency by which the composition is administered are well-known in the art and any suitable frequency of administration can be used within the context of the present invention (e.g., one 6 g dose per day or two 3 g doses per day) and over any suitable time period (e.g., a single dose can be administered over a five minute time period or over a one hour time period, or, alternatively, multiple doses can be administered over an extended time period). The composition of the present invention can be administered over an extended period of time, such as weeks, months or years. The composition can be administered in individual servings comprising one or more than one doses (individual servings) per day, to make a daily serving comprising the total amount of the composition administered in a day or 24 hour period.

Any suitable dose of the present composition can be used within the context of the present invention. Methods of calculating proper doses are well known in the art.

"Treatment" or "treating" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Prevent" or "preventing" refers to averting, stalling, stopping or hindering something from happening, including by advance action. There is overlap in treating and preventing.

"Effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

"Substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited. in any manner by the permissible substituents of organic compounds. Also, the terms "substitution" or "substituted with" include, the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"Alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six from one to four) carbon atoms.

"Akyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that, is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

"cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, sulfo-oxo, or thiol as described herein.

"Polyalkylene group" as used herein is a group having two or more $CH_2$ groups linked to one another. The polyalkylene group can be represented by a formula $—(CH_2)_a—$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1—OA^2$ or $-OA^1—(OA^2)_a-OA^3$, where "a" is an integer of from 1 to 200 and $A^1$, $A^2$, and $A^3$ are alkyl and/or cycloalkyl groups.

The terms "amine" or "amino" as used herein are represented by a formula $NA^1A^2A^3$, where $A^1$, $A^2$, and $A^3$ can be, independently, hydrogen or optionally substituted alkyl, cycloakyl, alkenyl, cycloalkenyl, alkynyl, cycloalkynyl, aryl, or heteroaryl group as described herein.

The term "hydroxyl" as used herein is represented by a formula —OH.

The term "nitro" as used herein is represented by a formula $—NO_2$.

Experimental Examples

Example 1

DIAMOND (Diet Induced Animal Model of Non-alcoholic fatty liver Disease) is a proprietary isogenic mouse strain that sequentially develops non-alcoholic fatty liver disease, non-alcoholic steatohepatitis, fibrosis, and hepatocellular carcinoma in response to a high-fat, high-sugar diet. Disease progression in the DIAMOND mice uniquely parallels human disease progression, including histopathology.

Twelve 8-wk old male DIAMOND mice were placed on ad libitum high fat diet (Harlan—ENVIGO TD.88317) and water containing glucose (18.9% w/v) and fructose (23.1% w/v); all mice remained on this diet throughout the study protocol. At 12 weeks of age, mice were divided into two groups: 1) 2-HOBA (n=6), and 2) vehicle controls (n=6). Animals in the 2-HOBA group received 2-HOBA in drinking water (1 g/L water with glucose and fructose). The vehicle control group received water without 2-HOBA (with glucose and fructose). Body weight and food intake were measured weekly. At –23 weeks of age, all animals underwent a glucose tolerance test (GTT) and MRI imaging to assess hepatic fat. For the GTT, animals were fasted for 12 hours and then glucose (2 g/kg bw of a 100 mg/mL glucose in sterile water) was administered by oral gavage. Blood was sampled at 0, 15, 30, 45, 60, 90, and 120 minutes after glucose administration and area under the curve was calculated. Animals were sacrificed at 24 weeks of age (12 weeks of 2-HOBA or vehicle treatment). Tissues and serum were collected for analysis.

Liver sections were stained with hematoxylin and eosin (for scoring of steatosis, hepatocyte ballooning, and inflammation) and Sirius red (for assessment of fibrosis). Scoring was performed in a blinded manner for steatosis, ballooning, inflammation, and necrosis using the following criterial, Steatosis (0-4): 0=<5%; 1=5-25%; 2=25-50%; 3=50-75%; 4=75-100%. Ballooning (0-3): 0=absent; 1=mild (focal involving fewer than three hepatocytes); 2=moderate (focal involving more than three hepatocytes or multifocal); 3=prominent (multifocal with more than two foci of three or more hepatocytes). Inflammation (0-4): 0=absent; 1=minimal (zero to one focus per 20× field); 2=mild (two foci); 3=moderate (three foci); 4=severe (four or more foci). Serum levels of glucose, alanine transaminase, and aspartate transaminase were measured. Liver mRNA expression was assessed via RT-qPCR for the following genes: Tnfa, Nlrpla, Il1b, Il18, Timp1, Colla1, ProCard, Nlrp3, Casp1, ProIl1b, Tgfb1, Bambi, Pdk4, and Gapdh. Two-tailed independent samples t-tests were used to compare endpoints between 2-HOBA and vehicle treated groups. Significance was set at $\alpha$=0.05.

Figure 1B:
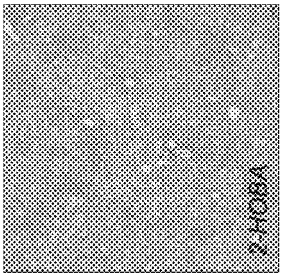

FIG. 1*a-b* shows Picosirius Red staining of control and 2-HOBA treated DIAMOND mouse livers. Scoring was defined on a scale of 0 to 4. All (4 out of 4) untreated mice had a fibrosis score of 1. Three of the 2-HOBA treated mice had a score of 0, while the remaining two had a score of 1.

Figure 2:
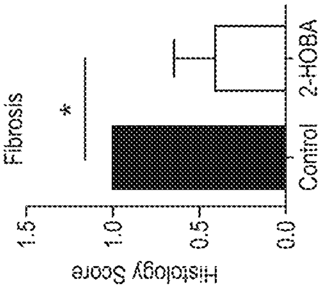
FIG. 2 is a graph depicting the fibrosis score in control and 2-HOBA treated mice.

FIG. 2 shows the fibrosis score in control and 2-HOBA treated DIAMOND mice. Despite similar degrees of hepatic steatosis and hepatocellular ballooning, the incidence of fibrosis was significantly lower in 2-HOBA compared to vehicle treated DIAMOND mice (p=0.03).

Figure 3:
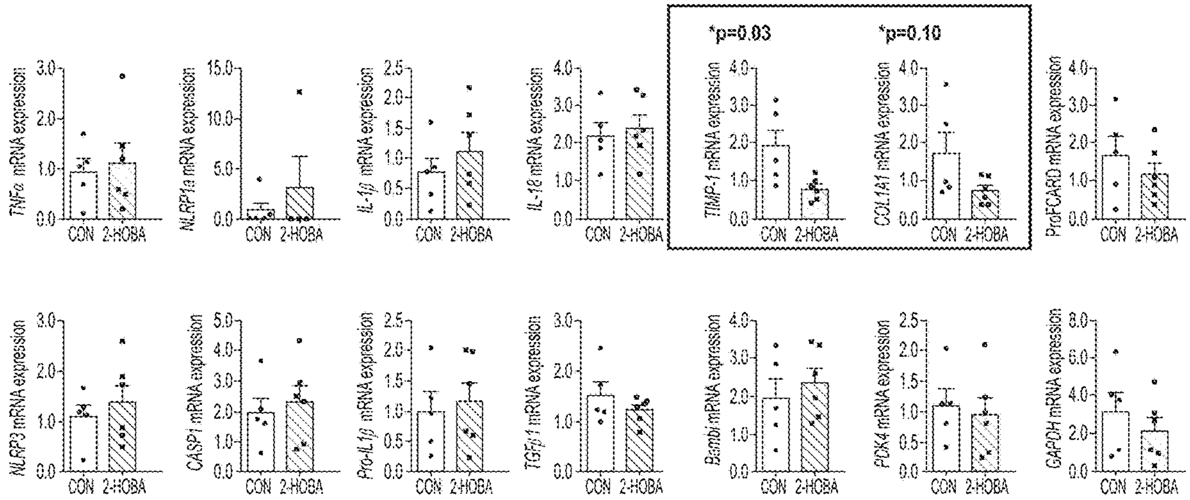
FIG. 3 depicts gene expression profiles by qRT-PCR.

FIG. 3 shows gene expression profiles by qRT-PCR, including measurements of key genes in hepatic inflammation and fibrosis progression. Elevated levels of tissue inhibitors of metalloproteinases (TIMP) inhibit metalloproteinases (MMP) which allows extracellular matrix proteins, such as collagens, to accumulate in liver tissue. 2-HOBA reduced liver Timp1 mRNA expression in DIAMOND mice, explaining the observed beneficial effect of 2-HOBA on fibrosis development. Further, Colla1 mRNA expression levels tended to be lower. This difference was not statistically significant (p=0.08).

The observed beneficial effects of 2-HOBA on liver fibrosis is unexpected and surprising as many NASH therapeutics have failed to improve fibrosis severity. Liver fibrosis severity is the only NASH factor that independently predicts liver-related morbidity and mortality, thus therapeutics capable of preventing or attenuating fibrosis development may dramatically improve outcomes in patients with NASH. The mechanism by which 2-HOBA is thought to be therapeutic for NASH is through the attenuation of inflammatory changes in the liver. Fibrosis, however, is a secondary stage pathogenesis with a different pathogenic mechanism. 2-HOBA independently attenuates hepatic fibrosis in the DIAMOND mice without altering markers of inflammation. As such, the results described herein are unexpected and surprising.

Example 2

γ-KAs induce activation of hepatic stellate cells (HSCs), which are the primary drivers of hepatic fibrosis. Preventing the activation of HSCs to a pro-inflammatory/pro-fibrogenic phenotype could inhibit the development of fibrosis in the liver. As transformation of HSCs into myofibroblast-like cells is considered essential for hepatic fibrosis, HSC activation will be measured using desmin, a marker of HSCs, and $\alpha$-smooth muscle actin (SMA), a marker of activated HSCs, by immunohistochemistry on fixed liver sections.

Experimental Design: All experiments will be performed on 24-h-serum-starved HSCs. To prevent γKA adduction to culture media components, experimental treatments will be initiated in amino-acid and lipid-free Hank's Buffered Salt Solution for the first 15 min of exposure. This exposure duration has previously been determined to be well-tolerated by human HSCs. Human HSCs will be pre-incubated with multiple doses (1-500 μM) of 2-HOBA or vehicle before being exposed to 0.5 μM 15-E2-IsoLG. Time course experiments with 2-HOBA and 15-$Ec_2$-levuglandin will be performed to determine the optimal durations for pre-treatment and 15-E2-IsoLG exposure. Following 15-E2-IsoLG exposure, media will be collected and cells will be washed and scraped for mRNA and protein analyses. Separate replicate plates will be prepared for ROS measurements.

Human HSCs: Human stellate cells will be obtained from ZenBio (Research Triangle Park, NC) and cultured in HSC complete medium (Iscove's Modified DMEM supplemented with 20% fetal bovine serum, 2 mM glutamine, 1× non-essential amino acids, 1 mM sodium pyruvate, and 1× antibiotic-antimycotic). All experiments will be performed on cells between passage 3 and 5.

15-$E_2$-isolevuglandin: Synthetic 15-E2-IsoLG in DMSO will be synthesized as previously described by our consultant.

Endpoints: RNA: The expression of selected transcripts related to fibrogenic activation, cytokine production, and adhesion molecules will be measured using $RT^2$ Profiler™ PCR Arrays (Qiagen, Frederick, MD) and single-gene probe-based qRT-PCR gene expression assays, as appropriate. Protein: Immunoblot analyses will be used to measure the content and activation status of key cell signaling pathways (ERK1/2, JNK, NFκB, and p38 MAPK). Cytokines: Inflammatory cytokine concentrations will be determined in media collected after incubation with 15-E2-IsoLG and 2-HOBA. ROS/RNS: Intracellular ROS/RNS formation will be measured using the 5-(and-6-)-carboxγ-2'-7'-dichlorodihydrofluorescein diacetate (Carboxγ-$H_2$) fluorescent probe (ThermoFisher Scientific). Total cell distribution will be visualized by staining nuclei with Hoechst 33342. Images will be acquired via fluorescence microscope.

Statistics: All experiments will be performed in triplicate. Data will be analyzed by one-way (dose) or two-way (dose×time) ANOVA (as appropriate for the design), with Bonferroni's multiple comparisons tests.

REFERENCES

1 Tilg, H. & Moschen, A. R. Evolution of inflammation in nonalcoholic fatty liver disease: the multiple parallel hits hypothesis. *Hepatology* 52, 1836-1846, doi:10.1002/hep.24001 (2010).

2 Brame, C. J., Salomon, R. G., Morrow, J. D. & Roberts, L. J. Identification of extremely reactive gamma-ketoaldehydes (isolevuglandins) as products of the isoprostane pathway and characterization of their lysyl protein adducts. *J. Biol. Chem* 274, 13139-13146 (1999).

3 Li, W. et al. Isolevuglandins covalently modify phosphatidylethanolamines in vivo: detection and quantitative analysis of hydroxylactam adducts. *Free Radic. Biol. Med* 47, 1539-1552 (2009).

4 Roychowdhury, S. et al. Formation of gamma-ketoaldehyde-protein adducts during ethanol-induced liver injury in mice. *Free Radic. Biol. Med* 47, 1526-1538 (2009).

5 Li, X. et al. Endoplasmic reticulum stress is the crossroads of autophagy, inflammation, and apoptosis signaling pathways and participates in liver fibrosis. *Inflamm Res* 64, 1-7, doi:10.1007/s00011-014-0772-y (2015).
6 Konishi, M. et al. Increased lipid peroxidation in patients with non-alcoholic fatty liver disease and chronic hepatitis C as measured by the plasma level of 8-isoprostane. *J Gastroenterol. Hepatol* 21, 1821-1825 (2006).
7 Davies, S. S. et al. Effects of reactive gamma-ketoaldehydes formed by the isoprostane pathway (isoketals) and cyclooxygenase pathway (levuglandins) on proteasome function. *FASEB J* 16, 715-717 (2002).
8 Guo, L. et al. Phosphatidylethanolamines modified by gamma-ketoaldehyde (gammaKA) induce endoplasmic reticulum stress and endothelial activation. *J. Biol. Chem* 286, 18170-18180 (2011).
9 Stavrovskaya, I. G. et al. Reactive gamma-ketoaldehydes formed via the isoprostane pathway disrupt mitochondrial respiration and calcium homeostasis. *Free Radic. Biol. Med* 49, 567-579 (2010).
10 Mont, S. et al. Accumulation of isolevuglandin-modified protein in normal and fibrotic lung. *Sci. Rep* 6, 24919 (2016).
11 Longato, L. et al. Reactive gamma-ketoaldehydes as novel activators of hepatic stellate cells in vitro. *Free Radic Biol Med* 102, 162-173, doi:10.1016/j.freeradbiomed.2016.11.036 (2017).
12 Estes, C., Razavi, H., Loomba, R., Younossi, Z. & Sanyal, A. J. Modeling the epidemic of nonalcoholic fatty liver disease demonstrates an exponential increase in burden of disease. *Hepatology*, doi:10.1002/hep.29466 (2017).
13 Wadden, T. A. et al. A two-year randomized trial of obesity treatment in primary care practice. *N Engl J Med* 365, 1969-1979, doi:10.1056/NEJMoa1109220 (2011).
14 Browning, J. D. et al. Prevalence of hepatic steatosis in an urban population in the United States: impact of ethnicity. *Hepatology* 40, 1387-1395, doi:10.1002/hep.20466 (2004).
15 Williams, C. D. et al. Prevalence of nonalcoholic fatty liver disease and nonalcoholic steatohepatitis among a largely middle-aged population utilizing ultrasound and liver biopsy: a prospective study. *Gastroenterology* 140, 124-131, doi:10.1053/j.gastro.2010.09.038 (2011).
16 Kim, C. H. & Younossi, Z. M. Nonalcoholic fatty liver disease: a manifestation of the metabolic syndrome. *Cleve. Clin. J. Med* 75, 721-728 (2008).
17 Pagano, G. et al. Nonalcoholic steatohepatitis, insulin resistance, and metabolic syndrome: further evidence for an etiologic association. *Hepatology* 35, 367-372 (2002).
18 Karlas, T., Wiegand, J. & Berg, T. Gastrointestinal complications of obesity: non-alcoholic fatty liver disease (NAFLD) and its sequelae. *Best Pract Res Clin Endocrinol Metab* 27, 195-208, doi:10.1016/j.beem.2013.02.002 (2013).
19 Ratziu, V., Bellentani, S., Cortez-Pinto, H., Day, C. & Marchesini, G. A position statement on NAFLD/NASH based on the EASL 2009 special conference. *J Hepatol* 53, 372-384, doi:10.1016/j.jhep.2010.04.008 (2010).
20 Charlton, M. R. et al. Frequency and outcomes of liver transplantation for nonalcoholic steatohepatitis in the United States. *Gastroenterology* 141, 1249-1253 (2011).
21 Fujii, M. et al. A murine model for non-alcoholic steatohepatitis showing evidence of association between diabetes and hepatocellular carcinoma. *Med. Mol. Morphol* 46, 141-152 (2013).
22 Asgharpour, A. et al. A diet-induced animal model of non-alcoholic fatty liver disease and hepatocellular cancer. *J Hepatol* 65, 579-588, doi:10.1016/j.jhep.2016.05.005 (2016).
23 Iyer, R. S., Ghosh, S. & Salomon, R. G. Levuglandin E2 crosslinks proteins. Prostaglandins 37, 471-480 (1989).
24 Murthi, K. K., Friedman, L. R., Oleinick, N. L. & Salomon, R. G. Formation of DNA-protein cross-links in mammalian cells by levuglandin E2. *Biochemistry* 32, 4090-4097 (1993).
25 Morrow, J. D. et al. A series of prostaglandin F2-like compounds are produced in vivo in humans by a non-cyclooxygenase, free radical-catalyzed mechanism. *Proc. Natl. Acad. Sci. U.S.A* 87, 9383-9387 (1990).
26 Salomon, R. G. & Miller, D. B. Levuglandins: isolation, characterization, and total synthesis of new secoprostanoid products from prostaglandin endoperoxides. *Adv. Prostaglandin Thromboxane Leukot. Res* 15, 323-326 (1985).
27 Bernoud-Hubac, N. et al. Low concentrations of reactive gamma-ketoaldehydes prime thromboxane-dependent human platelet aggregation via p38-MAPK activation. *Biochim. Biophys. Acta* 1791, 307-313 (2009).
28 Sullivan, C. B., Matafonova, E., Roberts, L. J., Amarnath, V. & Davies, S. S. Isoketals form cytotoxic phosphatidylethanolamine adducts in cells. *J. Lipid Res* 51, 999-1009 (2010).
29 Haukeland, J. W. et al. Systemic inflammation in nonalcoholic fatty liver disease is characterized by elevated levels of CCL2. *J. Hepatol* 44, 1167-1174 (2006).
30 Kojima, H. et al. Mitochondrial abnormality and oxidative stress in nonalcoholic steatohepatitis. *Alcohol Clin. Exp. Res* 31, S61-S66 (2007).
31 Elizondo, A. et al. Effects of weight loss on liver and erythrocyte polyunsaturated fatty acid pattern and oxidative stress status in obese patients with non-alcoholic fatty liver disease. *Biol. Res* 41, 59-68 (2008).
32 Wake, K. "Sternzellen" in the liver: perisinusoidal cells with special reference to storage of vitamin *A. Am J Anat* 132, 429-462, doi:10.1002/aja.1001320404 (1971).
33 Puche, J. E., Saiman, Y. & Friedman, S. L. Hepatic stellate cells and liver fibrosis. *Compr Physiol* 3, 1473-1492, doi:10.1002/cphy.c120035 (2013).
34 Marra, F. et al. Expression of monocyte chemotactic protein-1 precedes monocyte recruitment in a rat model of acute liver injury, and is modulated by vitamin E. *J Investig Med* 47, 66-75 (1999).
35 Parola, M. et al. Stimulation of lipid peroxidation or 4-hydroxynonenal treatment increases procollagen alpha 1 (I) gene expression in human liver fat-storing cells. *Biochem Biophys Res Commun* 194, 1044-1050, doi:10.1006/bbrc.1993.1927 (1993).
36 Parola, M. et al. HNE interacts directly with JNK isoforms in human hepatic stellate cells. *J Clin Invest* 102, 1942-1950, doi:10.1172/JC11413 (1998).
37 Zamara, E. et al. 4-Hydroxynonenal as a selective profibrogenic stimulus for activated human hepatic stellate cells. *J Hepatol* 40, 60-68 (2004).
38 Amarnath, V., Amarnath, K., Amarnath, K., Davies, S. & Roberts, L. J. Pyridoxamine: an extremely potent scavenger of 1,4-dicarbonyls. *Chem Res. Toxicol* 17, 410-415 (2004).
39 Davies, S. S. et al. Pyridoxamine analogues scavenge lipid-derived gamma-ketoaldehydes and protect against H2O2-mediated cytotoxicity. *Biochemistry* 45, 15756-15767 (2006).

40 Hagstrom, H. et al. Fibrosis stage but not NASH predicts mortality and time to development of severe liver disease in biopsy-proven NAFLD. *J Hepatol*, doi:10.1016/j.jhep.2017.07.027 (2017).

41 Neuschwander-Tetri, B. A. et al. Farnesoid X nuclear receptor ligand obeticholic acid for non-cirrhotic, non-alcoholic steatohepatitis (FLINT): a multicentre, randomised, placebo-controlled trial. *Lancet* 385, 956-965, doi:10.1016/50140-6736(14)61933-4 (2015).

42 Zagol-Ikapitte, I. A. et al. Determination of the Pharmacokinetics and Oral Bioavailability of Salicylamine, a Potent gamma-Ketoaldehyde Scavenger, by LC/MS/MS. *Pharmaceutics* 2, 18-29 (2010).

43 Kleiner, D. E. et al. Design and validation of a histological scoring system for nonalcoholic fatty liver disease. *Hepatology* 41, 1313-1321 (2005).

44 Amarnath, V., Amarnath, K., Masterson, T., Davies, S. & Roberts, L. J. A Simplified Synthesis of the Diastereomers of Levuglandin E2. *Synthetic Communications* 35, 397-408, doi:10.1081/SCC-200048945 (2005).

We claim:

1. A method for treating hepatic fibrosis in subject in need thereof, comprising:

identifying a subject in need of treatment for hepatic fibrosis;

administering to said subject an effective amount of at least one compound of the following formula:

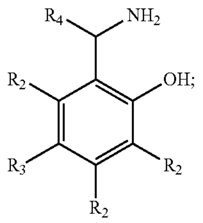

wherein:

$R_2$ is independently chosen from H, substituted or unsubstituted alkyl;

$R_3$ is H, halogen, alkyl, alkoxy, hydroxyl, nitro;

$R_4$ is H, substituted or unsubstituted alkyl, carboxyl; and pharmaceutically acceptable salts thereof;

wherein administration of the compound reduces liver Timp1 mRNA expression and attenuates hepatic fibrosis independent of reductions in hepatic inflammation.

2. The method of claim 1, wherein $R_2$ is independently chosen from H, ethyl, methyl.

3. The method of claim 1, wherein the compound is 2-hydroyxbenzylamine, methyl-2-hydroyxbenzylamine, ethyl-2-hydroyxbenzylamine.

4. The method of claim 1, wherein the compound is:

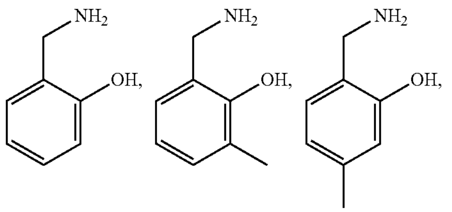

-continued

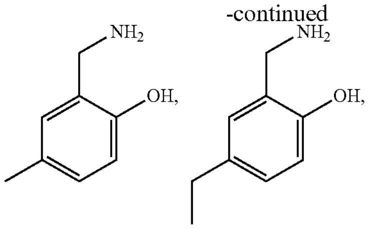

or

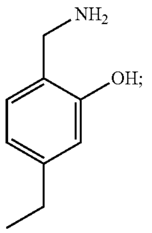

or a pharmaceutically acceptable salt thereof.

5. The method of claim 1, wherein the compound is:

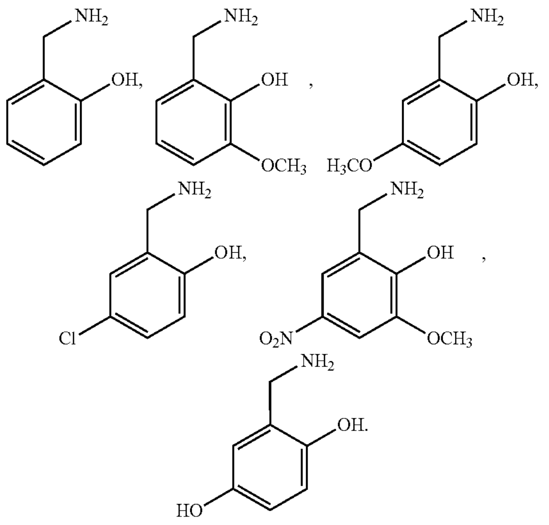

or a pharmaceutically acceptable salt thereof.

6. The method of claim 1, wherein the compound is:

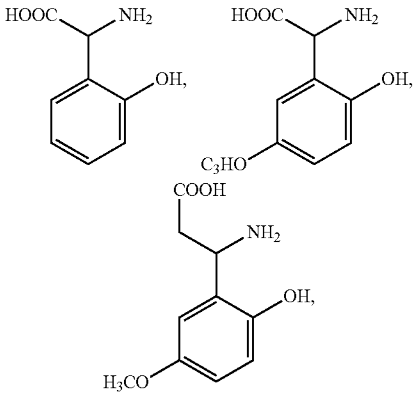

or a pharmaceutically acceptable salt thereof.

7. The method of claim 1, wherein the treating step inhibits the progression of hepatic fibrosis.

8. The method of claim 1, wherein the treating step attenuates the severity of hepatic fibrosis.

9. The method of claim 1, wherein the treating step mitigates the damaging effects of hepatic fibrosis in the subject.

10. The method of claim 1, wherein the compound or pharmaceutically acceptable salt thereof is administered in a composition that comprises said compound or a pharmaceutically acceptable salt thereof and a pharmaceutically acceptable carrier.

11. The method of claim 1, wherein the subject in need of treatment for hepatic fibrosis has or is at risk of developing hepatic fibrosis due to an etiology unrelated to alcohol consumption.

12. The method of claim 11, wherein the etiology is selected from the list consisting of nonalcoholic fatty liver disease (NAFLD), hepatitis, toxins, genetic conditions, autoimmune diseases and nonalcoholic steatohepatitis (NASH).

* * * * *